United States Patent
Cetingul et al.

(10) Patent No.: US 9,451,927 B2
(45) Date of Patent: Sep. 27, 2016

(54) COMPUTED TOMOGRAPHY DATA-BASED CYCLE ESTIMATION AND FOUR-DIMENSIONAL RECONSTRUCTION

(71) Applicant: Siemens Aktiengesellschaft, Munich (DE)

(72) Inventors: Hasan Ertan Cetingul, Baltimore, MD (US); Sandra Sudarsky, Bedminster, NJ (US); Indraneel Borgohain, East Windsor, NJ (US); Thomas Allmendinger, Forchheim (DE); Bernhard Schmidt, Fürth (DE); Magdalini-Charikleia Pilatou, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 99 days.

(21) Appl. No.: 14/525,360

(22) Filed: Oct. 28, 2014

(65) Prior Publication Data
US 2016/0113614 A1 Apr. 28, 2016

(51) Int. Cl.
G06K 9/00 (2006.01)
A61B 6/00 (2006.01)
A61B 6/03 (2006.01)
G06T 11/00 (2006.01)
G06T 7/00 (2006.01)
G06T 15/08 (2011.01)

(52) U.S. Cl.
CPC ............ *A61B 6/5288* (2013.01); *A61B 6/032* (2013.01); *A61B 6/486* (2013.01); *A61B 6/5205* (2013.01); *G06T 7/0012* (2013.01); *G06T 11/003* (2013.01); *G06T 15/08* (2013.01); *G06T 2207/10076* (2013.01); *G06T 2207/10081* (2013.01); *G06T 2207/10116* (2013.01); *G06T 2207/20108* (2013.01); *G06T 2207/30061* (2013.01); *G06T 2211/40* (2013.01)

(58) Field of Classification Search
None
See application file for complete search history.

(56) References Cited

U.S. PATENT DOCUMENTS

| 7,443,946 B2 | 10/2008 | Deller et al. |
| 8,526,702 B2 * | 9/2013 | Johnston ............... G06T 11/008 382/128 |
| 2002/0131544 A1 | 9/2002 | Aradate et al. |
| 2007/0237289 A1 | 10/2007 | Deller et al. |
| 2012/0059252 A1 | 3/2012 | Li et al. |
| 2012/0177271 A1 * | 7/2012 | Johnston ............... G06T 11/008 382/131 |
| 2013/0195341 A1 | 8/2013 | Liu et al. |

OTHER PUBLICATIONS

Belkin, Mikhail, and Partha Niyogi. "Laplacian eigenmaps for dimensionality reduction and data representation." Neural computation 15.6 (2003): 1373-1396.*

(Continued)

*Primary Examiner* — Tahmina Ansari

(57) ABSTRACT

Methods for computed tomography data-based cycle estimation and four-dimensional reconstruction are provided. A gated reconstruction is derived from CT data acquired without gating using an added artificial trigger. The resulting images for different slices are used to determine local or slice variations over time. The local variations over time for the various slices are combined to create a respiratory cycle signal. This respiratory cycle signal is used to bin the images for different phases, allowing four-dimensional CT reconstruction.

20 Claims, 4 Drawing Sheets

(56) References Cited

OTHER PUBLICATIONS

M. Belkin, et al., "Laplacian Eigenmaps for Dimensionality Reduction and Data Representation," Neural Computation, 15(6), pp. 1373-1396, 2002.

M. Georg, et al., "Manifold Learning for 4D CT Reconstruction of the Lung," Computer Vision and Pattern Recognition Workshops, pp. 1-8, 2008.

R. Li, et al., "4D CT sorting based on patient internal anatomy," Phys. Med. Biol. 54(15), pp. 4821-4833, 2009.

Y. Zhang, et al., "Resolution enhancement of lung 4D-CT data using multiscale interphase iterative nonlocal means," Med. Phys, 40(5), pp. 051916-1-051916-12, 2013.

G. Pierce, "Assessing and Improving 4D-CT Imaging for Radiotherapy Applications," Ph.D., Dissertation, The University of Western Ohio, pp. 1-183, 2011.

R. Zeng, et al., "Iterative Sorting for 4DCT Images Based on Internal Anatomy Motion," IEEE International Symposium on Biomedical Imaging, pp. 744-747, 2007.

Y. Zhang, et al., "Reconstruction of Super-Resolution Lung 4D-CT Using Patch-Based Sparse Representation," IEEE Conference on Computer Vision and Pattern Recognition (CVPR), pp. 925-931, 2012.

GE Medical Systems, LLC, 510(k) Premarket Notification Submission for Discovery CT590 RT/Optima CT580 with Deviceless 4D Option, pp. 1-10, 2014.

R. Zeng, et al., "Iterative sorting of four-dimensional CT images based on internal anatomy motion," Med. Phys. 35(3), pp. 917-926, 2008.

* cited by examiner

COMPUTED TOMOGRAPHY DATA-BASED CYCLE ESTIMATION AND FOUR-DIMENSIONAL RECONSTRUCTION

BACKGROUND

The present embodiments relate to medical imaging and, in particular, to surrogate-free four dimensional (4D) computed tomography (CT) reconstruction.

CT is often used for imaging tissues, such as lungs, that do not provide high contrast in MR images. Capturing lung dynamics due to patient respiration during the acquisition is crucial for accurately localizing and treating abnormalities, such as tumors, in the thoracic or abdominal regions. Clinical CT scanners acquire 4D CT data using one of two methods: low pitch helical or ciné acquisition sequences. In helical acquisitions, data are acquired while the table moves through the gantry. In ciné acquisitions, data are acquired in slabs that include only a small part of the body region under investigation. The de facto procedure in the clinic to "solve" this problem is to reconstruct 4D CT data by stitching together consecutive body segments. 4D CT imaging alleviates some of the problems associated with respiratory motion, improving the accuracy of radiation therapy. During a 4D CT scan, a large number of axial images are collected over several breathing cycles. These images are then sorted into a series of 3D volumes corresponding to different breathing phases. Inaccurate sorting often leads to motion and blurring artifacts in the reconstructed volumes.

Most 4D CT image reconstruction methods rely on external respiratory monitoring systems (e.g., bellows-based or real-time position monitoring (RPM) systems) to derive a signal for sorting the large number of images into different respiratory phases. It is assumed that the images within each phase bin were acquired at the same respiratory phase and are combined to form a 3D volume at that phase. This approach has several drawbacks. External respiratory surrogates are often expensive, inconvenient (e.g., requiring calibration) and time consuming. Moreover, mismatches between the external signal and the internal breathing motion may generate volumes suffering from imaging artifacts, especially during irregular breathing patterns.

Several free-breathing techniques have been proposed in the literature to improve 4D CT imaging, attempting to eliminate the need for external surrogates of respiratory motion. These methods may be computationally expensive, require manual intervention, such as to select a reference volume, and/or may fail to remove or sufficiently reduce artifacts.

BRIEF SUMMARY

By way of introduction, the preferred embodiments described below include methods, computer readable media, and systems for data-based cycle estimation for computed tomography (CT) reconstruction. A gated reconstruction is derived using an added artificial trigger with CT data acquired without gating. The resulting images for different slices are used to determine local or slice variations over time. The local variations over time for the various slices are combined to create a respiratory cycle signal. This respiratory cycle signal is used to bin the images into different phases, allowing four-dimensional reconstruction.

In a first aspect, a method is provided for data-based cycle estimation and computed tomography (CT) reconstruction. A patient is scanned with a computed tomography (CT) scanner without gating. A processor reconstructs CT images with trigger reference points added for a gated reconstruction. The trigger reference points are based on the parameters of the acquisition sequence, and the images represent each of a plurality of slices at different times. The patient's breathing cycle is derived from the images. The images are binned into breathing phases using the breathing cycle. A four-dimensional reconstruction of the patient is output as a function of the binned images for the breathing phases.

In a second aspect, a non-transitory computer readable storage medium has stored therein data representing instructions executable by a programmed processor for data-based cycle estimation and computed tomography (CT) reconstruction. The storage medium includes instructions for calculating an artificial trigger signal and reconstructing, with a CT system, CT images of slices from CT data of a patient; computing local respiratory signals for respective slices, with dimensionality reduction; selecting one of the slices as a reference; aligning the local respiratory signals of the slices to the local respiratory signal of the reference; calculating a global respiratory signal for the patient, the global respiratory signal being a function of the local respiratory signals after the alignment; assigning the CT images to inhalation and exhalation phases based on the global respiratory signal; and for at least one of the slices, generating a sequence of the CT images or formed images generated from the CT images, the sequence representing the patient through at least inhalation, exhalation, or both based on the assigning.

In a third aspect, a system is provided for data-based cycle estimation and computed tomography (CT) reconstruction. A CT scanner is configured to reconstruct a sequence of two-dimensional images over time for each of a plurality of axial planes. A processor is configured to calculate local variation through the sequence for each of the axial planes and to combine the local variations from different ones of the axial planes representing the same times. A result of the combining is an estimate of a cycle. The CT scanner is configured to generating a four-dimensional reconstruction for at least one of the axial or imaging planes using the estimate of the cycle.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Inspired from the preliminary results of the image-based approaches, a new image-based 4D CT reconstruction technique estimates a signal that is consistent with the patient's respiration. 4D CT reconstruction is performed by assigning axial images to respiratory phase bins using the estimated signal. Surrogate-free 4D CT reconstruction is provided. An image-based 4D-CT reconstruction technique accepts raw CT data acquired in helical or ciné mode. CT images are reconstructed based on artificial trigger time points, generating a representation of all available raw data in image space. The signal that is consistent with the patient's respiration is computed from the above-mentioned CT images. A 4D CT reconstruction is performed by assigning axial images computed from the acquired projection data to user-defined respiratory phase bins.

Accurate image guided radiation therapy may be provided. By estimating the respiratory signal from the acquired images, some of the disadvantages of using a surrogate may be overcome. By using the local-to-global process on imaging data calculated using an artificial trigger, 4D CT data may be generated with a reduced number of imaging artifacts as compared to other data-driven 4D CT reconstruction techniques. Fully automatic operation for 4D CT is provided, but user interaction may be allowed for parameter tuning.

Figure 1:
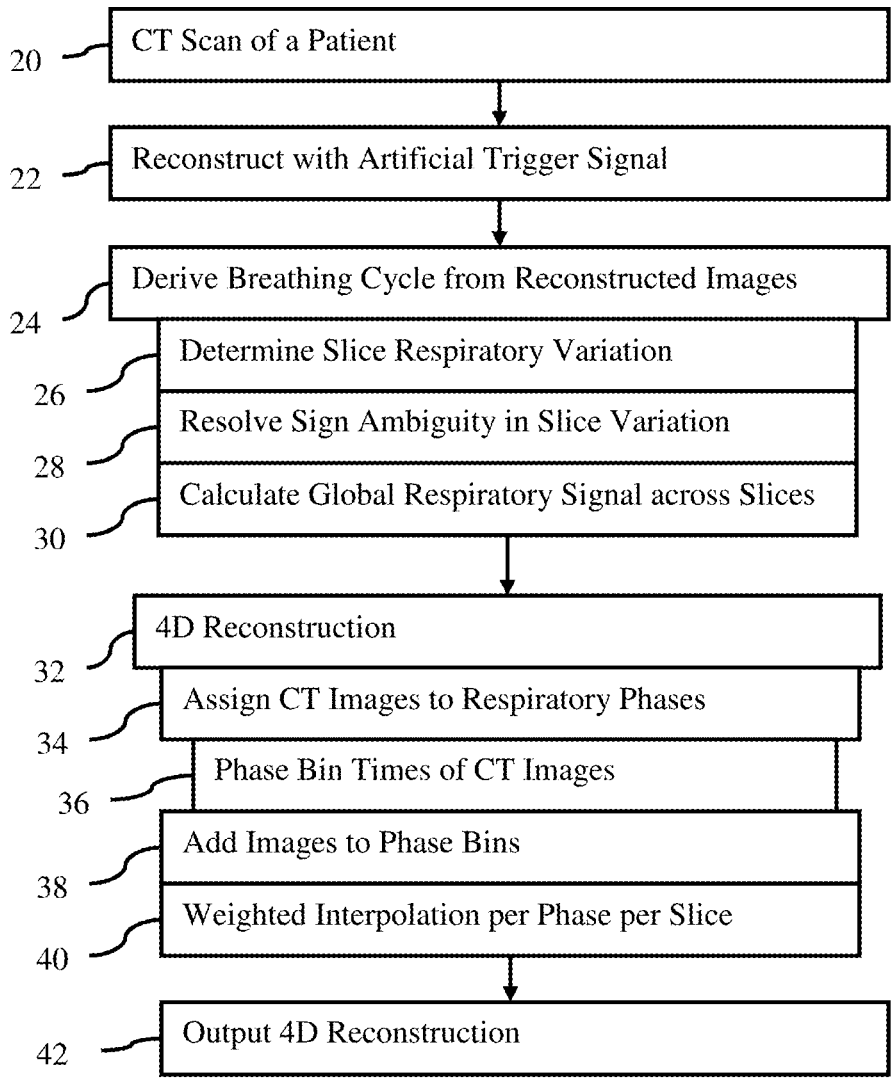
FIG. 1 is a flow chart diagram of one embodiment of a method for data-based cycle estimation for computed tomography (CT) reconstruction.

FIG. 1 shows one embodiment of a method for data-based cycle estimation for computed tomography (CT) reconstruction. In general, the method includes acts categorized into four stages: (1) reconstruction of CT images from raw data using an artificial trigger signal (e.g., act 22), (2) initialization and estimation of the local (respiratory) signals (e.g., act 26), (3) estimation of the image-based surrogate signal (global respiratory signal) (e.g., act 30), and (4) 4D CT reconstruction (e.g., act 32).

Additional, different, or fewer acts may be performed. For example, act 20 is not performed where the data itself is acquired by transfer or loading from memory. As another example, act 28 is not provided where determining the slice or local variation does not result in sign ambiguity. In yet another example, act 32 is provided with or without any combination of acts 34-40. There may be no output of the 4D reconstruction in other embodiments. Acts for using the 4D reconstruction for imaging and/or guiding therapy may be provided. Any combination of these differences may be used.

The method is implemented in the order shown or a different order. The acts are performed automatically by a CT scanner and processor. The CT scanner performs act 20. The processor, such as processor of the CT scanner or other processor, performs the other acts. For automated performance, the user causes the patient to be scanned or obtains scan data for the patient from a previous scan. The user may activate the process. Once activated, the method is performed without any user input. Other user input may be provided, such as for changing parameter values. Given the difficulty of interpreting a CT image, let alone many CT images, by a physician focused on treating a patient, the processor implementation assists the physician in a way not provided by manual operation. The technology of CT imaging and imaging to guide radiation therapy is improved by using the acts for 4D CT as performed by the CT scanner and/or processor.

In act 20, data representing a patient is obtained. A CT scanner or system scans the patient. Alternatively, a CT-like or other x-ray system is used. A source and opposing detector are moved by a gantry relative to a patient. During movement or at stoppage points over a range of movement, x-ray projection images are acquired. Any scanning sequence or approach may be used, such as a helical or ciné acquisition. The acquisition may be designed for any application, such as a torso scan covering from a patient's neck or shoulder region to the hips or lower torso. Greater or lesser extent of the scan may be provided.

The scanning occurs without gating. The timing of the scanning may be based on a breathing cycle in general, such as extending over a range of motion in a typical respiratory cycle. The patient's respiratory cycle may have been previously measured and used for planning and controlling the acquisition. The scan itself is not gated to the respiratory cycle. A surrogate signal, such as from a breathing belt or sensor, is not used to gate acquisition of the x-ray projections nor to gate timing of operation of the CT scanner. In alternative embodiments, gating is used.

In an alternative embodiment, the data is acquired by loading from memory. Data from a previously performed CT scan of the patient is stored in a memory, such as a picture archiving and communications system (PACS) database. The data is selected from the database. The data may be obtained by transfer, such as over a network or on a portable memory device.

The data represents the patient. Different projections through the patient at different angles and/or positions are provided. The timing, orientation, and spatial position for each projection relative to other projections are known. Due to the projection nature of x-ray imaging, the attenuation or other x-ray measured property of the different specific locations in the patient is not known without reconstruction.

In act 22, CT images of different planes through the patient are reconstructed by the CT system or a processor. Using the projection data, the processor solves for the attenuation or other characteristic through each of any number of planes or voxels distributed throughout the patient. In one embodiment, axial slices are reconstructed, but non-axial slices may be reconstructed in other embodiments. Any number of slices is provided, such as tens or hundreds. The slices are parallel, such as stacked along the axial direction of the patient. Alternatively, the slices are not parallel.

Trigger reference points are added to emulate or provide a gated reconstruction. While actual gating may not be used during acquisition, trigger points are added as artificial reference points. The trigger points are based on the parameters of the acquisition sequence, and are not derived from a patient breathing cycle measured during the acquisition of act 20 and/or at any other time. The trigger reference points are timed without reference to sensing of the respiratory cycle of the patient, at least during acquisition, but a patient specific measure of the respiratory cycle may be used (e.g., measured at a time other than during acquisition). The trigger references points may be based on an expected length of the breathing cycle for patients in general or the patient being scanned and the parameters of the acquisition sequence.

The cycle (C) of the artificial trigger signal is calculated from the parameters of the acquisition sequence; number of detector elements (N), rotation time ($r_t$) of the gantry and pitch (P). Specifically, $C=(r_t*(N-1))/(N*P)$, but other functions with the same or different group of parameters may be used. In case of a ciné acquisition, P is equal to unity and only one reference point $t_0$ at the start of the data acquisition range is required. The weighting of the data in the reconstruction starts at the time points $t_m=t_0+m*\phi$ for the image volume $V_m$, where m is an index starting at zero and increasing with a step of unity until all available data is covered and $\phi$ is the reconstruction angle. In case of a helical acquisition, multiple reference points $t^j$ are derived with $t^0=t_0$ and $t^{j+1}=t^j+dt$ where dt is derived from the parameters of the acquisition sequence. Based on these trigger points, the time points for weighting the reconstruction for the image volume $V_m$ are calculated as $t^j_m=t^j+m*\phi$. The number of phases for complete data coverage for helical or ciné acquisition is calculated as NPhases=ceil(dt/$\phi$).

Any CT reconstruction algorithm (e.g. filtered back-projection, iterative) may be used for the reconstruction of the CT images using an artificial trigger signal. The parameters of the acquisition sequence may be varied as well as the reconstruction angle $\phi$. In one embodiment, a CT reconstruction using the filtered back-projection method and based on an artificial trigger signal is used without 4D binning. For example, a reconstruction angle of 180 or 360 degrees is provided for multiphase reconstruction with temporal spacing of the added trigger reference points equal to the reconstruction angle.

The reconstruction provides CT images, such as CT images based on artificial trigger points, from the raw data. CT images are provided for each of a plurality of slices. For each slice, such as axially spaced slices, multiple CT images are provided. The CT images for each slice represent the slice at different times. Due to the parameters of the acquisition sequence and the reconstruction angle $\phi$, a number (e.g., twenty) of CT images are reconstructed for each slice over a range of times, such as over the one, two, or more breathing cycles established by the artificial trigger. As the CT scanner progresses in the scan of the patient, different slices have CT images for different times or ranges of times. Some slices may have CT images for overlapping ranges of times. Some slices may be spaced far enough apart that the CT images for one slice do not overlap in time for another slice. In one example embodiment, twenty or so (e.g., +/− five) CT images per slice are reconstructed over a single cycle of the artificial trigger. CT images are reconstructed for each of two hundred and fifty slices that cover the body region under investigation, with a temporal step size between images of 250 milliseconds. The total scanning time is 300 seconds. Other numbers or times may be used.

In act 24, the breathing cycle is derived from the CT images based on the artificial trigger. The images from one or more slices are used to determine the respiratory cycle. The determined respiratory cycle is the cycle that actually occurred during acquisition of the raw CT data. Rather than using the artificial timing, the actual breathing cycles and corresponding variations that occurred for the patient at the time or during acquisition is determined from the CT images.

In one embodiment represented in FIG. 1, the breathing cycle is derived by calculating a global respiratory cycle across slices in act 30 from respiratory variations occurring as determined in local regions, such as for one or more slices, in act 26. Other only global (e.g., across slices without separate determination of local variation) or only local (e.g., for one slice) may be used.

In act 26, a local signal variation is determined for each or a sub-set of the slices. The CT images representing a given slice at different times are used to find the local or slice variation for a single slice. A given local variation may be variation over a group of slices in other embodiments. A local respiratory signal is computed by a processor for each of all of or for a sub-set of axial slices, providing more than one local variation. The examples below will operate on one local variation for each slice.

Given the time series of images per slice, the images are organized or the timing labels are used. The individual images $\{I_{z;\ n}\}$ are organized according to the slice position and then according to the acquisition times in ascending order. For each slice, the CT images are labeled in temporal order. There is a one-to-one correspondence between the slice position (in mm) and the slice index, hereby denoted by z, yet this is not true for the acquisition time t. The acquisition time index, n=1,2, ..., N, where N is the number of images acquired for each slice, is used. The acquisition times of the $10^{th}$ image or other N of each slice, $\{I_{z;\ 10}: z=1,2, ..., Z\}$ might be different for different slices due to the nature of the CT acquisition. Instead, the temporal order is used rather than absolute time.

The slices for which the local variation is calculated are all slices or a sub-set. The processor or user may select the slices. In one embodiment, slices that have less than adequate temporal information for local respiratory signal estimation are eliminated automatically. For example, fewer than a threshold number (e.g., fifteen or fewer) of CT images may be available for a given slice due to the physical structure of the CT scanner. Such slices are often detected at the beginning or towards the end of the acquisition (neck or lower torso) and eliminated as "blocks" so that the remaining set of slices is spatially intact or contiguous (e.g., if slices z=98 and z=100 are found to be problematic in a set of 100 slices, the 3 slices z ∈ {98, 99, 100} are not considered in the analysis).

For user selection, a representation of available information may be provided. For example, the average-over-time CT volume is computed by the processor as $$\frac{1}{N}\sum_{n=1}^{N} I_{z;n}, \forall z,$$

for display and possible user interactions. The CT images from different times for a given slice are averaged or one selected. This results one CT image per slice, providing a volume. An image of the volume may be rendered for the user to identify spatial locations of interest. Some slices not associated with the spatial region of interest may be removed or not used for calculating the local respiratory signals. The user may select a slice coverage (i.e., between user-specified $z_{min}$ and $z_{max}$) and thus focus on a smaller region. The default coverage includes the axial slices remaining after any automated selection.

The average or sample volume may be used for defining a region of interest. For example, the volume is used to locate a slice through a larger portion of the lungs. Any CT image for the slice may be used for finding the ROI. In one approach, the CT image having the largest area of lung tissue is used. Such a slice may be automatically determined in other embodiments.

A CT image for the selected slice is used to define an automatically- or manually-drawn region of interest (ROI) large enough to cover lung/tissue/background borders or abdomen/background borders in an axial slice. Inclusion of ROI borders assists in the estimation and representation of the respiratory motion in lower-dimensional spaces.

The ROI is propagated to the CT images of other slices. For example, the coordinates of this ROI in one CT image is then applied to the CT images for all the axial slices. Alternatively, the ROI is determined separately for each slice and/or CT image. In yet other alternatives, no ROI is used.

Any variation calculation may be used. In one embodiment, a dimensionality reduction technique is used. Other approaches may include manifold learning, averaging or summation of values, or image similarity-based processing techniques (e.g., cross-correlation or minimum sum of absolute differences).

In dimensionality reduction, the dimensionality of the CT images is reduced. The CT image information of the ROI is vectorized. For example, a vector is provided for each CT image for a given slice, such as twenty vectors for the twenty CT images of a slice, where each vector includes the intensities of the CT image in the ROI. After the vectorization of the image information within the ROI (denoted as $\hat{I}$), a dimensionality reduction technique, such as Laplacian Eigenmaps (LEM) or Isomap, is applied to the matrix $[\hat{I}_{z;\,1}, \hat{I}_{z;\,2}, \ldots, \hat{I}_{z;\,N}]$. The dimensionality reduction provides the local variation signal. In the twenty CT image vector example, the local signal is amplitude (reduced intensities to a single value) as a function of CT image. The local signal is highly correlated with the respiratory dynamics observed at slice z.

Figure 2:
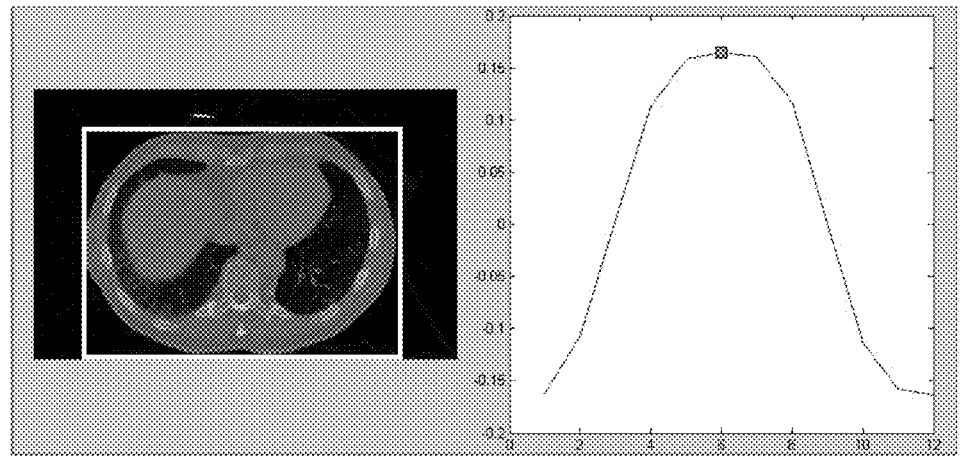
FIG. 2 shows an example CT image for a slice and a corresponding local respiratory signal for the slice.

The left side of FIG. 2 shows an example CT image of an axial slice, such as a reference slice used for setting the ROI (represented as a box). In this example, the CT image is an averaged over time CT image formed by averaging the twelve CT images for the slice. The ROI is a manually drawn ROI for the slice or as propagated from another slice. The graph on the right of FIG. 2 is the local variation signal given by LEM. The local respiratory signal provides amplitude as a function of time or CT image. In other embodiments, the local respiratory signal is represented using phase instead of amplitude.

LEM or other dimensionality reduction techniques may result in sign ambiguity. For example, the curve of FIG. 2 has a downward facing parabola shape, but the curve for other slices may have the inverse (e.g., upward facing parabola shape). For multiple cycle acquisitions per slice, the sine wave for one slice may be inverted or flipped by 180 degrees from another sine wave for another slice.

In act 28, the sign ambiguity of the local signal variations are resolved. Using one of the slices as reference and the corresponding local signal variation, the sign ambiguity is resolved across the slices of interest. Any slice may be used as the reference. In one embodiment, the slice is selected automatically by the processor or manually by an operator as a slice whose dynamics is consistent with the local signal. For example, the processor analyzes the average CT image for each slice to determine a lung area. The average CT image and corresponding slice with the greatest amount of lung is selected as the reference. Rather than a greatest, a threshold may be used to find the first slice processed with a certain lung area within the ROI. In other embodiments, the reference is selected using image similarity, such as selecting an image with the highest cross-correlation or similarity to other images. Manual selection may be used.

After selecting the reference slice, the local signals for other slices are aligned with the reference. The local signals are compared by correlation. Starting from the reference, the local signal of one or two adjacent slices is correlated with the reference and corrected, if appropriate. The corrected local signal is then correlated with the local signal of the next adjacent slice, and so on. If a local signal is found to be negatively correlated with the observed respiration of the reference or adjacent local signal (e.g., signal increases while lung volume decreases), the local signal is inverted. If positively correlated, then the local variation signal is maintained without inversion. This alignment resolves the sign ambiguity generated by LEM, so that a coherent breathing pattern and similar signal values are obtained across slices having CT images acquired at the same time instance (in HH:MM:SS). In other embodiments, another continuous or discrete signal processing technique than correlation is used to align local respiratory signals.

In act 30, a global respiratory signal is calculated for the patient. The global signal is calculated from two or more, such as all, of the local variation signals after aligning to resolve sign ambiguity. The global respiratory signal is calculated to be consistent with the patient's respiration during the acquisition.

Any function may be used to calculate the global respiratory signal from the local variations. For example, a temporally aligned average of the local signals is used. The amplitudes of the local signals corresponding to the same time instance are averaged. The average is calculated for each time increment over the entire acquisition time. The local signal for each slice begins at a different time than for other slices. By accounting for the temporal offset, the average may provide the global signal.

Figure 3:
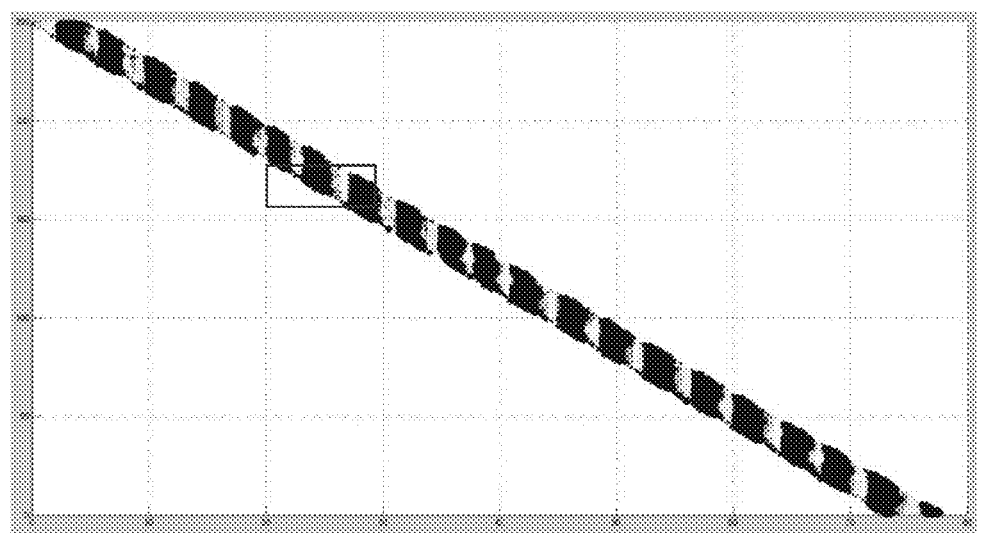
FIG. 3 shows an example bubble plot of local respiratory signals by slice and time.
Figure 4:
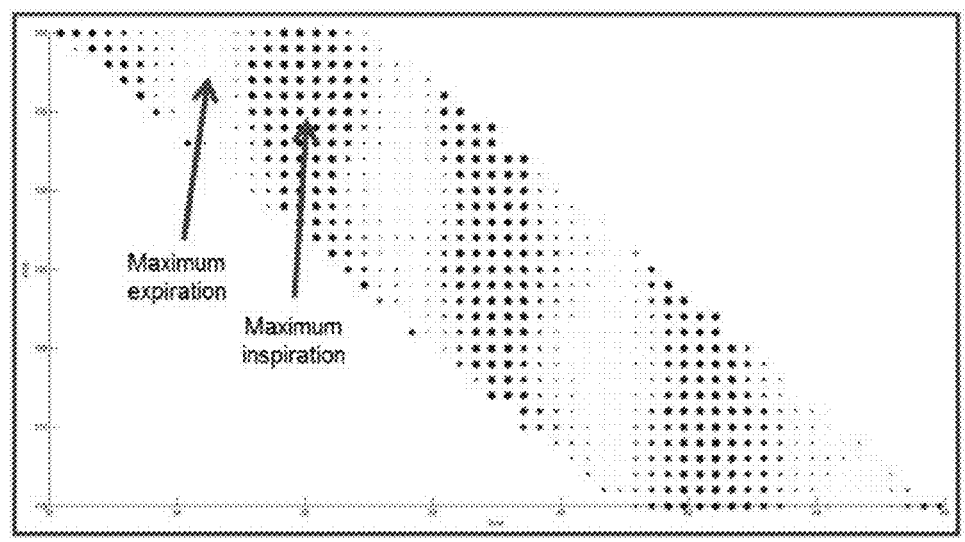
FIG. 4 shows an enlargement of a portion of the bubble plot of FIG. 3.

In one embodiment, a matrix of the slices as a function of time is formed from the local signal variations. The matrix has rows or columns corresponding to the slices between $z_{min}$ and $z_{max}$ and columns or rows corresponding to different acquisition times from the beginning to the end of the entire CT acquisition. The local signal values for a particular slice z (i.e., row) occupy N columns that correspond to the actual acquisition times of the images $\{I_{z;\,n}\}$ of that slice. FIG. 3 shows one example matrix as a bubble plot. FIG. 4 is a blow-up or expanded view of the rectangular box of FIG. 3 with times corresponding to inhalation and exhalation labeled. In the examples of FIGS. 3 and 4, vertical or y-axis is the slice and the horizontal or x-axis is the time. The local signal has amplitude values for the various CT images representing the slice at various times. In the examples of FIGS. 3 and 4, the amplitude of the local variation signal is represented by the size of the bubble. Viewing a row of bubbles for a given slice, the variation in bubble size along the row corresponds to the variation in amplitude of the local signal over the range of CT images for that slice. In the example of FIG. 4, seventeen or eighteen slices have CT images acquired at the same time (i.e., there is a seventeen to eighteen slice range for each time). Other matrix or non-matrix representations may be used. In yet other embodiments, the matrix is a visual representation to show the concept and is not specifically formed by the processor. Instead, the processor creates the global breathing signal from the local signals.

Figure 5:
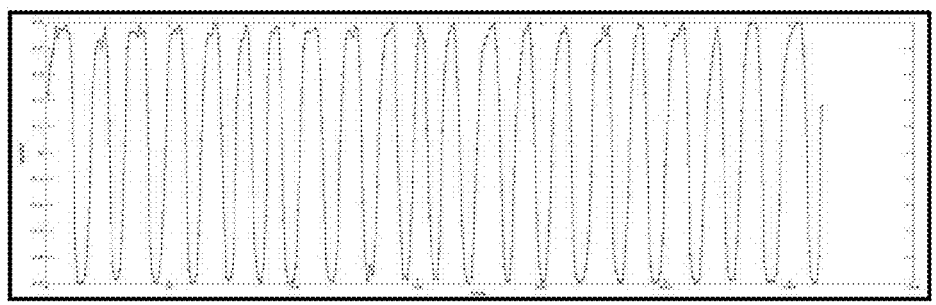
FIG. 5 illustrates an example respiratory signal as a function of time derived from the local respiratory signals of the example of FIGS. 3 and 4.

The local signals are combined across the slices for each of the times. For a given time, the local signal amplitude of the seventeen or eighteen slices of the example of FIGS. 3 and 4 (or other number in other examples) is averaged, summed, maximum selection, or otherwise combined. The local signals representing the same time are combined, such as by averaging. For example, the average signal values across the columns of the abovementioned matrix are computed to provide the image-based surrogate signal. FIG. 5 shows an example surrogate signal from the average of the FIG. 3 matrix. This image-based surrogate is the breathing cycle or global respiratory signal. The average over the slices plotted as a function of time indicates the respiration cycle. This signal correlates well or represents the true respiratory signal of the patient during the acquisition. The extrema represent peak inspiration (peak positive) and peak expiration (peak negative).

In some embodiments, the estimated global respiratory signal may be used as a surrogate to guide the reconstruction from raw projection data and generation of a new set of axial images that might better represent the patient's respiration. This can be considered as an iterative refinement of the acquired images and the estimated breathing cycle.

The surrogate signal (e.g., breathing cycle) and CT images are used for 4D CT in act 32. Rather than repeating reconstruction from raw projection data, the previously reconstructed CT images are temporally aligned relative to the slice and breathing cycle to complete reconstruction of the 4D CT.

In preparation for the 4D CT reconstruction, the image-based breathing cycle may be smoothed, such as low pass filtered. The extrema may be detected using any peak detection, such as sign change in the slope. The extrema are used to label the different times for the CT images as inhalation or exhalation. For example, times associated with upward slope of the cycle are inhalation, and times associated with downward slope of the cycle are exhalation.

The 4D CT is to provide CT images for slices or volumes representing different phases of the breathing cycle. Any division of the breathing cycle may be used, such as a pre-determined or user selected division. The breathing cycle is broken into different phases. For example, the cycle includes a full inhalation phase, a full exhalation phase, four partial inhale phases and four partial exhale phases (e.g., 0%, 20% inhale, 40% inhale, 60% inhale, 80% inhale, 100%, 80% exhale, 60% exhale, 40% exhale, 20% exhale, 0%). Each phase represents a range, such as 80% covering 71%-90%. Continuous phase bands are provided.

Due to the ungated acquisition, different CT images for a given slice represent different breathing phases. In act 34, the CT images are assigned to the inhalation and exhalation phases. The global respiratory signal indicates the phase for any given time and corresponding CT image.

The extrema of the calculated respiratory signal are analyzed, and the image acquisition times are labeled as either inhalation or exhalation. The times are used to determine to which phase each CT image belongs. In alternative embodiments, similarity-based processing is used to label the image acquisition times as inhalation or exhalation or to determine the phases to which the images belong.

The times and corresponding CT images are binned in act 36 into the different breathing phases of the breathing cycle. Different CT images and corresponding times belong to different inhalation, different exhalation, peak inhalation, or peak exhalation phases. The breathing cycle (e.g., FIG. 5) indicates the phase to which a given time belongs. For example, the axial CT images are assigned to user-defined or other defined respiratory phase bins. Each acquisition time is assigned to a breathing phase. Rather than using amplitude of the breathing signal, a phase representation may be used for assigning to the breathing phases.

The assignment may result in any number of CT images for a given slice at a given phase. For example, each slice is represented by K images (typically $K \in \{3,4,5\}$) for a breathing phase. If fewer than a threshold number of CT images are provided for a slice at a given phase, then images are added in act 38. "Missing" images in a particular respiratory phase are compensated for by using the available images.

The images to be added are from a different one of the breathing phases for the one of the slices (e.g., add a CT image from 40% or 80% inhale phase of slice three into 60% inhale phase of slice three), from a different slice for the one of the breathing phases (e.g., CT image from 40% inhale phase of slice two or three into 40% inhale phase of slice four), or from a same level of the one of the breathing phases with a difference in inhalation or exhalation (e.g., CT image from 40% inhale phase of slice three into 40% exhale phase of slice three). Where more than one CT image is to be added, combinations of the sources of CT images may be used. Other sources of additions of CT images may be used, such as adding in an average CT image.

Rather than adding a selected image, interpolation may be used to form the image for adding. For each slice that is represented with less than K images for a breathing phase, two images of the slice of interest that were acquired before and after the time instance at which the surrogate signal would have reached the assigned breathing phase level are identified. In other embodiments, the images for prior and after phases or opposing adjacent slices are identified. Then, the 2D deformation between these two images is computed using non-linear registration. Any affine or non-rigid transform may be used. The resulting deformation field is used to warp one of the images to have a new axial image at the time of interest.

In act 40, the binned and any added CT images for a given breathing phase of a given slice are combined. For example, the three to five CT images in slice three for 40% exhale phase are combined. The combination is repeated for the CT images of each phase within each slice.

Any combination may be used, such as selection, averaging, or weighted interpolation. The CT images of at least one of the slices representing a same respiratory phase are interpolated into a phase and slice specific image. A phase and slice specific image is provided for each of a plurality of respiratory phases of a given slice and for each of one or more slices.

For the weighted interpolation, the weights are inversely proportional to the differences between the signal values (e.g., time relative to phase) and the assigned breathing phase level. For example, the 60% phase band extends from 51% to 70%. The weight is greater for CT images acquired closer to the 60% timing and lesser for CT images acquired closer to the 51% and 70% timing. Any linear or non-linear function may be used for the weights.

In alternative embodiments, compressive sensing, ROI- or patch-based analysis, and/or non-linear interpolation are used to compute 2D images for each phase of each slice. These techniques may be used to increase the out-of-plane resolution of the image volumes created by combining the CT images of the phases.

After combination (e.g., weighted interpolation), the resulting CT image represents the slice at a particular breathing phase. The combination is provided for each of the phases over a portion or all of at least one breathing cycle. For three-dimensional imaging or to provide a volume, the combination is performed for the multiple adjacent slices. Interpolated images for a given phase are created for each of a plurality of slices. To show motion or adding a temporal component, volumes are created for each of multiple phases. The volume over time provides 4D CT reconstruction.

Further processing may be provided. For example, volumes or images for a given slice may be interpolated in time. New or additional volumes or images for a slice are interpolated from volumes or slices adjacent in time. Deformable registration may be used to create additional volumes or slices. If the user requests or there are not adequate CT images to create an image for a slice or a volume, the replacement is formed from interpolated or combined images adjacent in time or space.

Other processing may include temporal or spatial filtering. Segmentation, detection, edge enhancement or other processes may be performed.

In act 42, a 4D CT reconstruction of the patient is output. The created volumes for a plurality of phases are output. Alternatively, surface or projection rendering is performed, and the resulting images are output as the 4D CT. Using the binned CT images for the different breathing phases as detected from the images, the 4D CT volumes or images rendered from the volumes are output. The result is a sequence of formed images or volumes. The sequence represents the patient through part or all of the breathing cycle, such as through inhalation, exhalation, or both.

Figure 6:
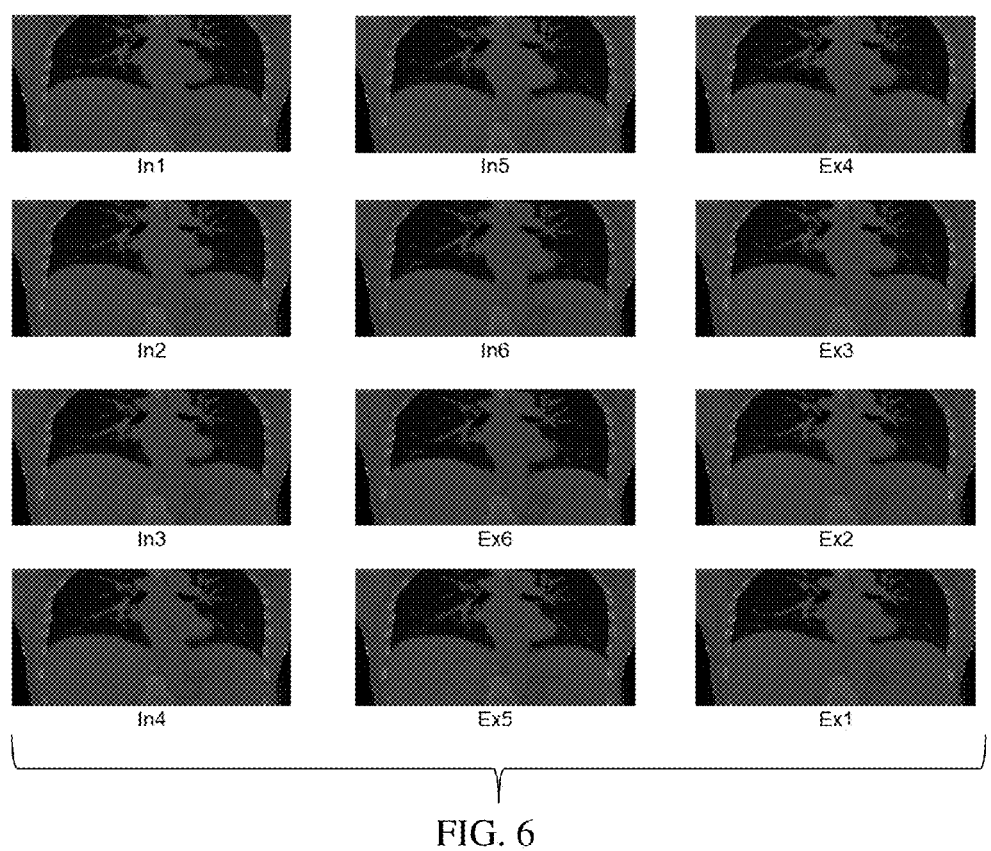
FIG. 6 shows example 4D CT images aligned by phase based on the respiratory signal of FIG. 5.

In alternative embodiments, images representing a single slice over time are output. The 4D CT reconstruction provides for volumes or slice images over part or all of the cycle. FIG. 6 shows a coronal view of the 4D CT reconstruction using twelve breathing phases (Inhale 1 (In 1)-Inhale 6 (In 6) and Exhale 1 (Ex1)-Exhale 6 (Ex 6). No post-processing has been performed to further smooth the volumes. The 4D CT reconstruction can be visualized from each imaging plane (axial, coronal, sagittal) by showing the temporal evolution (based on the estimated breathing cycle) of the rendered images on those planes.

The rendered images are displayed at a same time or in sequence. The rendered images includes pixel intensities mapped to display values. The images are of the torso of the patient, such as showing the lungs, surrounding anatomy, and any foreign structures. Other information may be included, such as graphic overlays or image data from other modalities of imaging.

In alternative or additional embodiments, the volumes or images of the 4D CT reconstruction are used for quantification. A volume, area, length, curvature, or other quantity is calculated.

Figure 7:
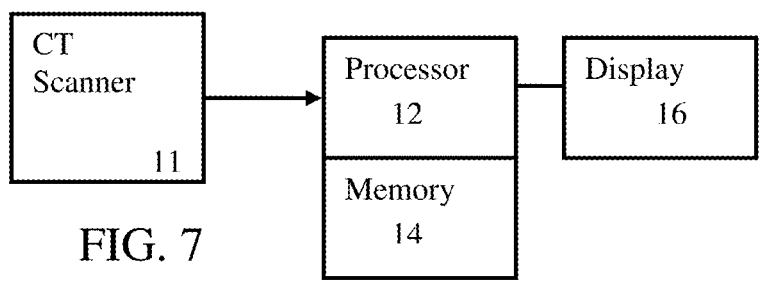
FIG. 7 is a block diagram of one embodiment of a system for data-based cycle estimation for computed tomography (CT) reconstruction.

FIG. 7 shows a system for data-based cycle estimation for computed tomography (CT) reconstruction. The system includes a medical CT scanner 11, a processor 12, a memory 14, and a display 16. The processor 12 and the memory 14 are shown separate from the medical CT scanner 11, such associated with being a computer or workstation apart from the medical CT scanner 11. In other embodiments, the processor 12 and/or memory 14 are part of the medical CT scanner 11. In alternative embodiments, the system is a workstation, computer, or server for data-based cycle estimation for computed tomography (CT) reconstruction from data acquired by a separate system in real-time or using previously acquired patient-specific data stored in a memory. For example, the medical CT scanner 11 is provided for acquiring projection data, and a separate database, server, workstation, and/or computer is provided for determining the breathing cycle for 4D CT.

Additional, different, or fewer components may be used. For example, a user interface is provided for entering an ROI, selecting slices (e.g., spatial extent of slices or analysis), inputting breathing phase resolution (e.g., number of phase bins), or configuring rendering.

The computing components of the system, such as the medical CT scanner 11 and/or the processor 12 are configured by hardware, software, and/or circuit design to perform calculations or other acts. The computing components operate independently or in conjunction with each other to perform any given act, such as the acts of FIG. 1 or the method. The act is performed by one of the computer components, another of the computing components, or a combination of the computing components. Other components may be used by the computing components to scan or perform other functions.

The medical CT scanner 11 is any now known or later developed CT System. An x-ray source and detector are connected on opposite sides of a patient area to a gantry. The gantry includes a motor for moving the source and detector about the patient for helical or ciné scanning. The medical CT scanner 11 is configured to acquire projection images from different angles and/or positions relative to the patient. The data is acquired by scanning the patient without input from a breathing sensor. Non-gated scanning is provided.

The CT scanner 11 includes a processor, such as the processor 12 or other processor, for reconstructing a sequence of two-dimensional images over time for each of a plurality of axial planes. The raw data from the scanning is reconstructed into pixel or voxel values representing attenuation or other x-ray characteristics at different locations or points in the patient. The reconstruction is from projection data of the CT scanner.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical data. The processor 12 is a single device, a plurality of devices, or a network. For more than one device, parallel or sequential division of processing may be used. Different devices making up the processor 12 may perform different functions, such as creating the curved reformation sub-volume by one processor and rendering by another processor. In one embodiment, the processor 12 is a control processor or other processor of the medical CT scanner 11. The processor 12 operates pursuant to stored instructions to perform various acts described herein, such as acts of FIG. 1.

The processor 12 is configured to calculate local variation through the sequence for each of the axial planes. For example, the local variation is for a region of interest using dimensionality reduction. As another example, a sum of intensities, average intensity, or other value from the data of the reconstructed axial plane over time is calculated.

The processor 12 is configured to combine the local variations from different of the axial planes. The local variations are temporally aligned so that the amplitude or phase of the variation from different axial planes representing the same time are combined. Any combination may be used, such as an average or sum. The result of the combination of the temporally aligned local variations from different axial planes is an estimate of the breathing cycle. This estimated breathing cycle represents the inhalation and/or exhalation of the patient during the un-gated acquisition of the raw projection data from the patient.

The CT scanner 11, the processor 12, or the CT scanner 11 using an included processor 12 creates a 4D CT reconstruction using the estimated breathing cycle. Reconstructed images are binned into phases based on the timing of acquisition. For each slice, reconstructed images are labeled as being for different phases using the derived breathing cycle. For a given phase, the reconstructed images are combined, providing one image for each phase for a slice. Images are provided through the phases for the different slices, providing a 4D CT reconstruction. The 4D CT reconstruction represents a volume of the patient at different times. The formed images for the axial over plane are created by binning the reconstructed images from the original scan by phase and combining the images of the bins.

The processor 12 is configured to render an image or sequence of images from the volume of a phase or from volumes from different phases. Surface or projection rendering is performed. Alternatively, a multi-planar reconstruction is created from the volume or volumes over time. Where formed images are provided for a single plane, then a sequence of two-dimensional images are provided.

The display 16 is a CRT, LCD, plasma, projector, printer, or other output device for showing an image. The display 16 displays an image or sequence of images of the 4D CT reconstruction. An image or images for a given axial plane may be alternatively or additionally displayed. A multi-planar reconstruction or volume rendering of a sequence of the volume through multiple breathing phases is displayed. A sequence of images may be displayed as a 4D CT movie.

In one embodiment, the display 16 is configured to display the local variation signals and/or the estimated breathing cycle. The global breathing signal is displayed with the sequence of images or movie, showing the breathing cycle phase for each image of the sequence as the image is displayed. The estimated breathing cycle may be displayed alone or without 4D CT.

The memory 14 is a buffer, cache, RAM, removable media, hard drive, magnetic, optical, database, or other now known or later developed memory. The memory 14 is a single device or group of two or more devices. The memory 14 is within the system 11, part of a computer with the processor 12, or is outside or remote from other components.

The memory 14 stores the data representing the patient. The data represents the torso of the patient, but other regions may be alternatively or additionally represented. The data is raw CT data, such as projection data. The data may be reconstructed CT images representing different axial or other planes. The data represents a three-dimensional region. Any format may be used, such as voxels interpolated to a three-dimensional grid or data representing parallel or non-parallel planes. The data may be segmented, such as including locations known to be for different anatomy. The memory 14 stores data resulting from processes, such as storing local variation signals, a matrix, and/or the global variation signal.

The memory 14 is additionally or alternatively a non-transitory computer readable storage medium with processing instructions. The memory 14 stores data representing instructions executable by the programmed processor 12 for data-based cycle estimation for computed tomography (CT) reconstruction. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for data-based cycle estimation and computed tomography (CT) reconstruction, the method comprising:

scanning a patient with a computed tomography (CT) scanner without gating;

reconstructing, with a processor, CT images with trigger reference points added for a gated reconstruction, the trigger reference points based on an expected cycle length of a breathing cycle, the images representing each of a plurality of slices at different times;

deriving the breathing cycle from the images;

binning the images into breathing phases using the breathing cycle;

generating a four-dimensional reconstruction of the patient as a function of the binned images for the breathing phases.

2. The method of claim 1 wherein scanning comprises scanning without the gating from a breathing sensor.

3. The method of claim 1 wherein reconstructing comprises multiphase reconstructing with a temporal spacing due to the added trigger reference points equal to a reconstruction angle.

4. The method of claim 1 wherein deriving comprises determining, for each of the slices, a local signal variation from the images of the different times for the respective slice.

5. The method of claim 4 wherein determining the local signal variation comprises representing the images in a lower dimensional space.

6. The method of claim 5 further comprising resolving sign ambiguity of the local signal variations across slices using one of the local signal variations as the reference.

7. The method of claim 4 wherein deriving further comprises forming a matrix of the slices as a function of time from the local signal variations, and temporally averaging the local signal variations across multiple slices, providing an estimate of the breathing cycle.

8. The method of claim 1 wherein binning comprises dividing the breathing cycle into different breathing phases and assigning images to the breathing phases.

9. The method of claim 8 further comprising interpolating the images in each of the breathing phases for each of the slices, resulting interpolated images for the breathing phases for each slice comprising the four-dimensional reconstruction.

10. The method of claim 9 further comprising:
adding one or more of the images for one of the breathing phases for one of the slices, the one or more images added from a different one of the breathing phases for the one of the slices, from a different slice for the one of the breathing phases, or from a same level of the one of the breathing phases with a difference in inhalation or exhalation.

11. In a non-transitory computer readable storage medium having stored therein data representing instructions executable by a programmed processor for data-based cycle estimation and computed tomography (CT) reconstruction, the storage medium comprising instructions for:
reconstructing, with a CT system, CT images of slices from CT data of a patient;
computing local respiratory signals for respective slices using dimensionality reduction;
selecting one of the slices as a reference;
aligning the local respiratory signals of the slices to the local respiratory signal of the reference;
calculating a global respiratory signal for the patient, the global respiratory signal being a function of the local respiratory signals after the alignment;
assigning the CT images to inhalation and exhalation phases based on the global respiratory signal; and
for at least one of the slices, generating a sequence of the CT images or formed images created from the CT images, the sequence representing the patient through at least inhalation, exhalation, or both based on the assigning.

12. The non-transitory computer readable storage medium of claim 11 wherein reconstructing comprises reconstructing with an added trigger reference point timed without reference to sensing of a respiratory cycle of the patient.

13. The non-transitory computer readable storage medium of claim 11 wherein computing comprises computing the local respiratory signals with the dimensionality reduction comprising Laplacian Eigenmaps, the local respiratory signals comprising amplitude or phase as a function of image where multiple of the images are acquired for each slice.

14. The non-transitory computer readable storage medium of claim 11 wherein selecting comprises selecting as a function of an amount of lung represented in the CT images of each of the slices, and wherein aligning comprises inverting the local respiratory signals of at least another one of the slices.

15. The non-transitory computer readable storage medium of claim 11 wherein calculating comprises averaging local signal values across the slices for each of a plurality of times, the average as a function of the time comprising the global respiratory signal for the patient.

16. The non-transitory computer readable storage medium of claim 11 wherein assigning comprises dividing the times into inhalation and exhalation phases as a function of extrema of the global respiratory signal and binning the times into different phases of inhalation and different phases of exhalation.

17. The non-transitory computer readable storage medium of claim 11 wherein generating comprises interpolating the CT images of the at least one of the slices representing a same respiratory phase into one of the formed images for each of a plurality of respiratory phases.

18. A system for data-based cycle estimation and computed tomography (CT) reconstruction, the system comprising:
a CT scanner configured to reconstruct a sequence of two-dimensional images over time for each of a plurality of axial planes; and
a processor configured to calculate local variation through the sequence for each of the axial planes and to combine the local variations from different of the axial planes representing the same times, a result of the combining comprising an estimate of a cycle;
(original) wherein the CT scanner is configured to generate a four-dimensional reconstruction for at least one of the axial planes using the estimate of the cycle.

19. The system of claim 18 further comprising a display configured to display the four-dimensional reconstruction.

20. The system of claim 18 wherein the processor is configured to calculate the local variation for each of the axial planes with dimensionality reduction.

* * * * *